US010413722B2

(12) United States Patent
Peled

(10) Patent No.: US 10,413,722 B2
(45) Date of Patent: Sep. 17, 2019

(54) PELVIC MUSCLE EXERCISER

(71) Applicant: Simona Peled, Hod HaSharon (IL)

(72) Inventor: Simona Peled, Hod HaSharon (IL)

(*) Notice: Subject to any disclaimer, the term of this patent is extended or adjusted under 35 U.S.C. 154(b) by 0 days.

(21) Appl. No.: 15/737,430

(22) PCT Filed: Jun. 19, 2016

(86) PCT No.: PCT/IL2016/050651
§ 371 (c)(1),
(2) Date: Dec. 18, 2017

(87) PCT Pub. No.: WO2016/203485
PCT Pub. Date: Dec. 22, 2016

(65) Prior Publication Data
US 2018/0185641 A1 Jul. 5, 2018

(30) Foreign Application Priority Data
Jun. 18, 2015 (IL) .......................................... 239549

(51) Int. Cl.
*A61N 1/36* (2006.01)
*A61N 1/05* (2006.01)
(Continued)

(52) U.S. Cl.
CPC ........ *A61N 1/36007* (2013.01); *A61B 5/0004* (2013.01); *A61B 5/1104* (2013.01);
(Continued)

(58) Field of Classification Search
CPC combination set(s) only.
See application file for complete search history.

(56) References Cited

U.S. PATENT DOCUMENTS 87,734 A * 3/1869 Van Camp ................ C10F 5/00
44/490
4,106,489 A * 8/1978 Martin ................... A63B 23/20
482/122
(Continued)

FOREIGN PATENT DOCUMENTS

AU 5472180 7/1981
CN 2668099 1/2005
(Continued)

OTHER PUBLICATIONS

Oldham, Herbert and McBride, Evolution of a New Disposable "Tampon Like" Electrostimulation Technology (Pelviva) for the Treatment of Urinary Incontinence in Women; A 12-Week Single Blind Randomized Controlled Trial, Wiley Periodicals Inc., 2012, United Kingdom.

*Primary Examiner* — Sean P Dougherty
(74) *Attorney, Agent, or Firm* — Robert G. Lev

(57) ABSTRACT

The present invention is directed to a device which may be used to interactively exercise pelvic muscles. This is expected to prevent the need for more intrusive surgical procedures, to improve the life of women and men that suffer from incontinence, to help women strengthen their pelvic muscles after birth to enable subsequent vaginal births rather than caesarean sections. The invention relates to a pelvic muscle exercise monitor that is a suppository/tampon type internal unit that may be placed within either the rectum or the vaginal canal and which sends signals to a remote receiver, typically a smart phone, but possibly a dedicated device or a computer.

21 Claims, 2 Drawing Sheets

(51) Int. Cl.
*A61B 5/22* (2006.01)
*A63B 23/20* (2006.01)
*A61N 1/375* (2006.01)
*A61N 1/372* (2006.01)
*A61B 5/00* (2006.01)
*A61B 5/11* (2006.01)

(52) U.S. Cl.
CPC ............... *A61B 5/22* (2013.01); *A61B 5/227* (2013.01); *A61N 1/05* (2013.01); *A61N 1/0521* (2013.01); *A61N 1/36* (2013.01); *A61N 1/36003* (2013.01); *A61N 1/37247* (2013.01); *A63B 23/20* (2013.01)

(56) References Cited

U.S. PATENT DOCUMENTS

| | | | |
|---|---|---|---|
| 5,800,501 A | 9/1998 | Sherlock | |
| 5,865,715 A * | 2/1999 | Wallick | A63B 23/20 482/121 |
| 6,370,912 B1 * | 4/2002 | Sutton | A44C 15/0045 482/105 |
| 6,406,411 B1 * | 6/2002 | Guagliano | A61B 5/227 482/121 |
| 6,562,018 B1 * | 5/2003 | Russell | A63B 23/20 604/105 |
| 6,752,749 B2 * | 6/2004 | Stein | A63B 23/20 482/121 |
| 2002/0169056 A1 * | 11/2002 | Ross | A61B 5/227 482/121 |
| 2003/0087734 A1 * | 5/2003 | Kring | A63B 23/20 482/112 |
| 2006/0036188 A1 | 2/2006 | Hoffman et al. | |
| 2006/0064038 A1 * | 3/2006 | Omata | A61B 5/103 600/587 |
| 2009/0171144 A1 | 7/2009 | Squicciarini | |
| 2009/0281397 A1 | 11/2009 | Lavoisier | |
| 2010/0051036 A1 * | 3/2010 | Kushnir | A63B 21/06 128/834 |
| 2010/0174218 A1 | 7/2010 | Shim | |
| 2015/0196802 A1 | 7/2015 | Siegel | |
| 2016/0279469 A1 * | 9/2016 | Rose | A61B 5/1107 |
| 2018/0185641 A1 * | 7/2018 | Peled | A61N 1/3756 |

FOREIGN PATENT DOCUMENTS

| | | |
|---|---|---|
| DE | 102012109409 | 5/2014 |
| EP | 2708187 | 3/2014 |
| GB | 2408953 | 3/2005 |
| KR | 101219990 | 7/2008 |
| SK | 113-2001 | 8/2002 |

\* cited by examiner

PELVIC MUSCLE EXERCISER

BACKGROUND

Weak pelvic muscles cause various problems such as incontinence. Women, especially after vaginal child birth, often have weakened vaginal muscles and suffer from urine leakage, particularly whilst coughing or sneezing. The condition is well established, and various types of exercise treatment have been proposed.

Both men and women may suffer from rectal incontinence and may need to exercise and strengthen rectal muscles.

Early crude devices such as those described in U.S. Pat. No. 1,928,893 titled "Vaginal and Rectal Exerciser" (from 1933) and U.S. Pat. No. 5,865,715 titled "Contraction resistance vaginal muscle exerciser" which describes a device somewhat reminiscent of a clothes-peg, are handheld spring devices that provide a counter force for the patient to overcome. Such devices exert a dilation force on the vagina that the patient tries to overcome. They are operable by the patient in private, but the handles protrude from the body so the device cannot be used discretely throughout the day. Such devices are also not calibrated.

An alternative approach is vaginal weight lifting. Essentially the patient tries to vaginally retain bulbs of different shapes, sizes and weights. Sometimes the weights are attached to a tail that protrudes from the vaginal opening. The idea is to train the vaginal tract to contract to apply a clamping pressure on the tampon, to overcome different weights that attempt to pull the tampon out of the body. The Guinness World Record for vaginal weightlifting is held by a physiotherapist called Tatyana Kozhevnikova who specializes in this physiotherapeutic treatment who dead-lifted a 14 kg kettle-bell.

U.S. Pat. No. 6,562,018 to titled "Pelvic floor muscle exerciser" describes a system that does not use weights but which utilizes an egg shaped tampon for insertion into the vaginal canal and a protruding tail that the patient pulls on to apply a force for the vaginal muscles to overcome. This system does not rely on gravity and so has greater flexibility and may be used by women who are immobilized.

USSN 2005/130818 to Karol describes a set of such exercisers with heads of different sizes, and different weights, and a tail protruding from the body. The weights are all within the head. The device is unitary which means less likely to break within the body. With reference to claim 34-37 thereof, it seems that the tail has different knobs diameters, or markings for noting depth of penetration and claim 57 teaches a stop to prevent over insertion. The head of the device may gradually or abruptly taper towards the tail and this affects the ease of retaining. The patient can switch devices to one more difficult to retain. An elbow sleeve may be used to fold the protruding tail to lie along the body, enabling the device to be retained whilst doing other things. Furthermore, this enables the patient to note twitching of the tail as the pelvic floor muscles are contracted.

More sophisticated systems use hydraulic or pneumatic systems to apply a dilation force on a tampon like insert These enable the patient's resistance to be monitored using a pressure gauge.

U.S. Pat. No. 6,752,749 to Stein describes introducing a phallic shaped plug into the vagina or anus, and a both springy type exercisers (FIGS. 38 to 43) and the egg shaped head of an insert (FIG. 23). Also described, in FIGS. 35 to 37, is a phallus with fluid filled balloons along the shaft such that external pressure on a reservoir of fluid causes the walls of the phallus are caused to dilate. FIG. 24 shows syringes and bulbs that can be used to adjust the pressure.

USSN 2003/0087734 to Kring et al. teaches an inflatable insert that may be inflated with liquid of air, and which is provided with a pressure gauge. The degree of inflation of the insert may be measured as well as pressure thereon exerted by the pelvic muscles.

U.S. Pat. No. 4,167,938 titled "Exerciser for vaginal muscles" describes yet another pneumatic/hydraulic system.

USS 2003/087734 titled "Vaginal-pelvic muscle exerciser and birthing trainer" describes a device for insertion into the birth canal of a female user. The device comprises an asymmetrical, inflatable, bulb defining an outer surface, the bulb sized and shaped so as to define a crease along at least a portion of the surface adapted to be placed in registry with the user's urethra when the bulb is inflated, the bulb further sized and shaped to contact the bulbocavernous facia, pubococcygeal facia and illiococcygeal facia when inflated, and means for inflating and deflating the bulb.

CN2668099 seems to work by pressure and to remote controlled. It is an external device that fits over the vaginal area and not an internal tampon.

CN203154731 titled Vaginal muscle contraction exerciser is a utility model for a vaginal muscle contraction exerciser which comprises a cylindrical hollow shell, a connecting plate arranged on the front section of the shell and provided with a through hole, an exercising rod with the rear end connected with the connecting plate and extending along the axial direction of the shell to the outer side of the front end of the shell, a cervix uteri tray arranged at the front end of the exercising rod, a piston mechanism arranged inside the shell to block communication of a front cavity and a rear cavity which are formed by dividing of the piston mechanism, and a handle mechanism connectedly sleeved on the shell and pulling the piston mechanism to move along the axial direction of the shell through ropes. The sealing ring is arranged at the edge of the front end of the shell. The vaginal muscle contraction exerciser is simple in structure and ingenious in design, a closed space is formed in a woman's vagina by the sealing ring and the cervix uteri tray, and the piston mechanism is controlled by a handle to be in reciprocating motion to reduce or restore air pressure of the closed space to force vaginal muscles to contract or extend along with the piston mechanism, so that muscle strength of the vaginal muscles is improved, sexual experience of a man and the woman in the sexual life is improved, and husband-wife affection is stabilized.

Although the discussion so far has related to women and urinary incontinence, men (and women) suffer from similar rectal problems and involuntary passing of stools can occur.

Using such devices to exercise the vaginal wall and the pelvic muscles has various disadvantages. Firstly, the patient needs to work with a therapist, whether a doctor, nurse or physiotherapist and this adds to the cost of such treatments. Secondly, many such treatments are designed for use in a clinic or surgery. The patient has to make an appointment and to exercise during the appointment slot Women with active lives and busy schedules find it difficult to attend such appointments. Also, because of menstruation, women may not be available for such appointments. Furthermore, due to scheduling and cost issues the series of treatments is generally short and inadequate. Additionally, it will be appreciated that many women feel exposed and embarrassed when undergoing such treatments, even in the presence of female medical personnel and clinicians.

A recent paper, titled "Evaluation of a new disposable "tampon like" electrostimulation technology (Pelviva®) for the treatment of urinary incontinence in women: a 12-week single blind randomized controlled trial" by Oldham J, Herbert J, McBride K. Neurourol Urodyn. 2013 June; 32(5): 460-6. doi: 10.1002/nau.22326. Epub 2012 Sep. 28, reports the results obtained using a disposable tampon which vibrates to 'exercise' or stimulate' the vaginal muscle. The device stimulates the vaginal muscles and provides pelvic floor muscle exercise for treatment of urinary incontinence in women.

Some success has been claimed for this system. The problem is that muscle stimulation by vibration is not what happens in everyday life. It does not simulate the muscles relaxing during coughing or sneezing that results in unpleasant and potentially embarrassing urine leakage.

The device described exercises the pelvic muscles for the woman and may indeed tone them. It does not address the issue of incontinence as a result of coughing or sneezing. It does not train the woman to use her muscles more effectively.

Although the discussion so far has related to women and urinary incontinence, men (and women) suffer from similar rectal problems and involuntary passing of stools can occur.

There is a need for a device that is discrete and that may be used to train the vaginal and rectal muscles. Such a device should not require hooking up to external machines in a clinic.

There are a plethora of mobile phone applications for exercise training, monitoring blood pressure, heart rate and other vital statistics. For example, KR 101219990 titled "Portable Occupational Therapy Apparatus and Method for Hand Rehabilitation, Apparatus Including Smart Phone Application for the Occupational Therapy" describes a smart-phone that may be used for physiotherapy. The organ exercised in this publication is the hand.

USSN 2013/296,963 describes a system and method for treating erectile dysfunction in males. It provides stimulation from a smart-phone application and uses erotic imagery on the smart-phone together with stimulation to train and tone the male's muscles.

German patent application DE 102012109409 is directed to an adult toy, specifically to a vibrator, that consists of a housing, a silicone sleeve connected with the housing, an electric motor that serves as an oscillator, an energy storage and a control unit A wireless data communication device is provided with a data storage unit for storing data and with a non-contact switch element. The control unit is arranged to transfer stored data to a remote device and to receive data from the remote device. The non-contact switch element is arranged to activate and to deactivate functional states of the vibrator. A silicone sleeve is provided over the housing, electric motor, energy storage and control unit. The device described is more or less phallic shaped and may be controlled by a mobile phone or a computer, enabling an operator to stimulate someone remotely over an internet link.

Although the telecommunication is described as being two-way, it seems that the intention is that pictures may be taken with a camera on the device and sent to the remote operator who can control the vibration of the device via a two-way communication with a remote controller. The remote controller (two-way) may be a smart-phone.

Although, it can be used within the vagina and not only externally, it is clear that the application contemplated is a masturbatory device, and a tampon like device for positioning within the vaginal cavity and leaving there whilst the patient goes about her daily activities is not intended.

Slovak Patent Application No. SK1132001A3 to Švec František, Nitra-Zobor, S K et al. titled "Booster of Pelvic Muscles and Constrictor Muscles of Urethra" describes a system for strengthening pelvic muscles and constrictor muscles of the urethra. The system includes an applicator which is connected with the muscle activity booster and logical unit. Data is sent to a computer, which displays the actual status and the process of set up data on computer keyboard, while the cover of the applicator with conductive electrode including the shield of the applicator, connected by a connecting ring through the gasket, together with the control chip and the source form an independent unit with an appendage that may be manipulated.

The device described is a sort of tampon that provides an electronic stimulating signal to the pelvic muscles. It thus offers a method of treatment that is wholly unnatural.

There is a need for a system and method for training the vaginal and rectal muscles that does not require hooking up to external machines in a clinic, that is discrete and which enables the patient to actively and willfully practice tensing muscles and obtaining feedback that she is doing so correctly. During strenuous workouts in the gym such as sit-ups and the like, many women apply a downward pressure on the pelvic floor when they should really be applying an upwards pressure to prevent involuntary urine release. It would be useful to train the pelvic muscles at odd times of the day, such as in bed, in the office, whilst relaxing or whilst undergoing strenuous exercise.

SUMMARY OF THE INVENTION

The present invention is directed to providing a system and method for training the pelvic muscles that overcomes the above detailed disadvantages.

It is an aim of the invention to provide an apparatus, a system and method for training the pelvic muscles that can be operated at the patient's convenience with respect to where the patient is.

It is an aim of the invention to provide an apparatus, a system and method for training the pelvic muscles that can be operated at the patient's convenience with respect to when such training occurs.

The apparatus, system and method should preferably be usable anywhere and everywhere, such as whilst training in the gym, sitting at a computer, walking, lying down or doing housework.

The apparatus, system and method should preferably be usable without the need for external assistance. However, it is useful if the apparatus, system and method can be used during a consultation session with a medical professional.

The apparatus, system and method should be feminine and discrete. It should be personal.

Preferably the cost of such an apparatus, system and method should be affordable so that people of all socio-economic levels can use it and that health funds and the legislative can consider subsidizing or providing freely within the range of medical treatments.

A first aspect is directed to a system for pelvic exercising by a user, the system comprising: an internal unit and a receiver device; the internal unit being substantially cylindrical and having a length of 3 to 8 cm and a diameter of between 1 and 3 cm, for positioning within a body cavity of the user; and comprising at least one pressure sensor and a transmitter within a housing; the receiver device comprising a GUI, a processor, a signal receiver, a memory, a power supply and an operating program, such that the receiver device receives data from the internal unit and displays information to the user.

Typically, the internal unit further comprises a flexible tail to one end of the internal device for withdrawal of the internal device from the body cavity.

Optionally, the flexible tail serves as an antenna for the transmitter.

In typical applications, the body cavity is a rectum or a vaginal canal.

Preferably, the housing comprises a biocompatible water proof polymer such as neoprene, silicone, latex or artificial rubber, for example. Typically, the internal unit further comprises a battery.

Optionally, the at least one pressure sensor of the internal unit is a piezoelectric sensor configured to detect pressure applied to said one end of the internal unit.

In some embodiments, the at least one pressure sensor of the internal unit is a piezoelectric sensor configured to detect pressure applied to an opposite end to said one end of the internal unit Preferably the internal unit further comprises a second pressure sensor of the internal unit configured to detect pressure applied to an opposite end of the internal unit.

In some embodiments, the system further comprises an anchor for attaching to the user, said internal unit further comprising a distance sensor for monitoring separation of the anchor from the internal unit.

In some embodiments, the anchor is attachable by an adhesive strip to a buttock or a navel.

In some embodiments, the anchor is attachable by a vacuum sucker to a buttock or a navel.

In other embodiments, the internal unit further comprises a movement sensor for monitoring movement along the vaginal canal. Such a movement sensor may comprise a light emitting diode and corresponding light sensor. In some embodiments, the movement sensor is an IC for an optical mouse.

Optionally, the internal unit further comprises an E M S. (Electrical Muscle Stimulation) system.

Typically, the internal unit is substantially cylindrical and has a length of 3-8 cm and a diameter of between 1 and 3 cm, for positioning within a body cavity of a user; and comprises at least one pressure sensor, a transmitter within a housing for communication with a receiver device.

Optionally, the internal unit further comprises a flexible tail attached to a first end of the internal device for withdrawing the internal device from the body cavity.

Optionally, the pressure sensor is positioned at a first end of the internal unit Alternatively, the pressure sensor is positioned at a second end of the internal unit.

In preferred embodiments, a first pressure sensor is positioned at a first end of the internal unit a second pressure sensor is positioned at a second end of the internal unit. The pressure sensor is a load cell.

In some embodiments, the pressure sensor is a piezoelectric pressure sensor configured to detect radial compressive forces around circumference of the internal unit.

In some embodiments, the pressure sensor is piezoelectric pressure sensor configured to detect forces on an end of the internal unit.

Typically, the internal unit is housed in a housing comprising a biocompatible water proof polymer.

Typically, the housing comprises neoprene, silicone, latex or artificial rubber.

In preferred embodiments, the internal unit further comprises a battery.

In some embodiments, the battery is rechargeable by induction.

In some embodiments, the internal unit comprises a distance sensor for monitoring a distance separating the internal unit from an anchor external to the user.

Typically such an anchor is attached to a position on an anatomy of the user.

Alternatively, the internal unit comprises a movement sensor for monitoring movement along a body cavity.

In some embodiment, the movement sensor comprises a light emitting diode and corresponding light sensor.

Optionally, the internal unit further comprising an E.M.S. (Electrical Muscle Stimulation) system.

Typically, the internal unit that is substantially cylindrical and has a length of 3-8 cm and a diameter of between 1 and 3 cm, for positioning within a body cavity of a user; and comprising at least one pressure sensor, a transmitter within a housing for communication with a receiver device.

A third aspect is directed to a receiver device comprising a GUI, a processor, a signal receiver, a memory, a power supply and an operating program, such that the receiver device is configured to receive data signal from an internal unit within a rectum or a vaginal canal of a user and to process such data and display information to the user.

Typically, the data signals comprise data from at least one pressure sensor of the internal unit.

Optionally, the data signals comprise data corresponding to a distance of the internal unit from an anchor positioned on external anatomy of the user. In some embodiments, the data signals comprise data corresponding to an absolute movement of the internal unit within a body cavity.

Optionally, the receiver device further comprises a transmitter for transmitting signals for activating an E.M.S. (Electrical Muscle Stimulation) system in the internal unit.

The receiver device of claim 34 may be a smart phone programmed with an application.

A fourth aspect is directed to a method of exercising a pelvis of a user comprising positioning an internal unit comprising at least one pressure sensor and a transmitter within a rectum or vaginal canal of a user; transmitting data from the internal unit to a receiver device comprising a GUI, a processor, a signal receiver, a memory, a power supply and an operating program, and processing such data to display information to the user regarding pressure on the internal unit.

Preferably, the internal unit comprises two pressure sensors, one at each end, and the data displayed includes pressure differences between contraction forces applied to each end.

Optionally, the internal unit further comprises a distance sensor for monitoring distance between the internal unit and an external anchor attached to anatomy of the user for monitoring movement of the internal unit with respect to the external anchor.

Alternatively, the internal unit further comprises a movement sensor for monitoring movement of the internal unit within a body cavity and the method comprises monitoring movement within the body cavity and displaying information for the user on the receiving unit.

In some embodiments, the internal unit further comprises an E.M.S. (Electrical Muscle Stimulation) system and the method comprises stimulating the muscular wall of the body cavity around the internal unit.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice. In the accompanying drawings.

DESCRIPTION OF PREFERRED EMBODIMENTS

Figure 1:
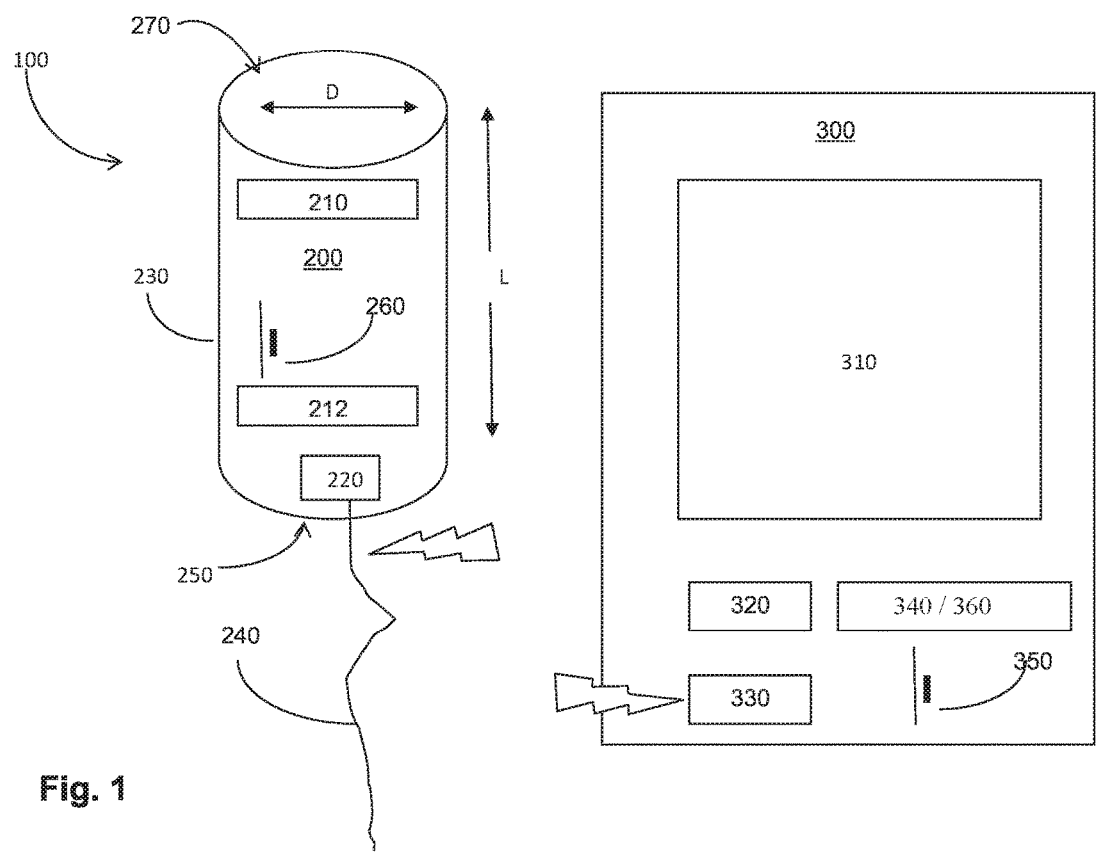
FIG. 1 is a schematic block diagram of a system of one embodiment of the invention.

The present invention is directed to a device which may be used to interactively exercise pelvic muscles. This is expected to prevent the need for more intrusive surgical procedures, to improve the life of women and men that suffer from incontinence, to help women strengthen their pelvic muscles after birth to enable subsequent vaginal births rather than caesarean sections.

Embodiments of the invention relate to a pelvic muscle exercise monitor that is a suppository/tampon type internal unit that may be placed within either the rectum or the vaginal canal and which sends signals to a remote receiver, typically a smart phone, but possibly a dedicated device or a computer. The internal unit resembles a tampon and may be retained within the vaginal canal for hours or even days. It is not weighted with external weights and is of a size and dimensions similar to conventional menstruation tampons, and so is not unpleasant or uncomfortable. The internal unit communicates with a receiver device and provides feedback to the user, typically via the graphic user interface GUI of the receiver device, which may be a dedicated device but is typically a smart phone with an appropriate program (App).

The internal unit contains sensors that are able to detect external pressure and preferred embodiments are able to do detect pressure differences from the radial pressure at the lower end and that at the higher end, to detect a pressure that may act to cause the internal unit to travel deeper into the vaginal canal or the rectum.

Strain gauges such as piezoelectric sensors may be used. A typical range is from under 2 microvolt where the vaginal muscles are relaxed, reaching as high as 80 micro-Volts for fully tensed muscles. The stresses may be displayed in micro-Volts or transposed and displayed in mm of mercury, Pascals, pounds per square inch, or any other numeric, qualitative scale after appropriate calibration. For physiotherapists and medical personnel, absolute numbers have some value. For patients, a descriptive display such as weak, strong, recovering from birth, healthy, etc. or a graphic display which may be descriptive, such as a graphical representation of a section through the vaginal canal with internal device in place, or analogous, such as an image of balloons or a cartoon character may be preferred. One commercially available load cell that may be considered is a 1000 BF-1 K Precision Pressure Resistance Strain Gauge 1000 ohm Sensor. Such devices are comparatively cheap and typically cost about $1.5 per unit.

In some embodiments an external anchor is attached to the user, for example to her navel. The external anchor can communicate with the internal unit thereby obtaining information regarding the separation of the internal unit and the external anchor. This information may be displayed on the GUI of the receiver device.

An alternative and better way for monitoring movement is for the internal unit to be provided with a light emitting diode (LED) and a corresponding sensor such as those used in optical computer mice. The LED and corresponding sensor enable small movements to be tracked.

By way of enablement only, an example of a commercially available IC offering the appropriate functionality is the ADNS2620 Optical Mouse Sensor. This is an easy to use entry level, small form factor optical mouse sensor intended for computer mice this allows for more compact and cost-effective optical mouse designs. The ADNS2620 is based on optical navigation technology, which measures changes in position by optically acquiring sequential surface images (frames) and mathematically determining the direction and magnitude of movement. It is housed in an 8-pin staggered DIP format and has a resolution of 400 counts per inch with rates of motion up to 12" per second and measure a mere 12.5 mm×10 mm so is fully compatible for use in intravaginal sensors. It has no mechanical moving parts, allows complete 2D Motion Sensing, offers a programmable frame speed of up to 3000 fps, gives accurate motion up to 12 fps, has a 400 dpi resolution.

It is, of course, immaterial if the distance is calculated by the receiver device (such as a mobile phone), the anchor or the internal unit Typically raw data regarding relative pressure at lower and upper parts of the internal unit and anchor-internal unit separation are transmitted to the smart phone. There, a dedicated Application processes the data and provides feedback to the user in real time as to whether or not pressure is applied to the internal unit and whether that pressure is applied evenly or mostly to the top or bottom areas of the internal unit, and whether the internal unit is moving nearer or away from the external anchor. In this manner, the user may obtain feedback whilst exercising to ensure that she is raising her pelvic floor correctly.

It will be appreciated that the internal unit transmits information to the receiver device. The internal unit is not programmed to vibrate or to take pictures but to simply report its position or change of position and pressures thereon.

Although the receiver device may be a dedicated device, typically it will be a smart phone or may be mobile or desktop computer. Typically it will include a signal receiver for communication with the internal unit and optionally with the anchor. Preferably the communication is by a wireless communication protocol such as Bluetooth. The receiver device further includes a graphic user interface such as a screen and keys or a touch screen, a processor and a memory for storing programming instructions. The programming instructions may be provided in the form of an application and the receiver device may be a smart-phone. Smart phones are fairly ubiquitous and have all the desired functionality.

With reference to FIG. 1 a schematic block diagram of a system of one embodiment of the invention is shown.

The system 100 provides a means for teaching and for monitoring the effectiveness of pelvic exercising by a user. The system 100 consists of an internal unit 200 and a receiver device 300. The internal unit 200 is substantially cylindrical and has a length L of 3 to 10 cm and a diameter D of between 1 and 4 cm. It may have flat or domed ends, for example. Internal device is thus similar to a menstrual tampon and may be positioned within the vaginal canal of a user. It includes at least one pressure sensor 210 and a transmitter 220 within a housing 230.

The internal unit 200 communicates with a receiver device 300 that typically has a visual display 310 that may be a graphic user interface GUI, a processor 320, a signal receiver 330, a memory 340, a power supply 350 and an operating program 360, such that the receiver device 300 receives data from the internal unit 200 and displays the information on the GUI 310 to the user.

Typically, the internal unit 200 further comprises a flexible tail 240 attached to one end 250 of the internal device 200 for withdrawal of the internal device 200 from the vaginal canal or another body cavity such as the rectum, for example.

Optionally, the flexible tail 240 serves as an antenna for the transmitter 220. Optionally, the housing 230 comprises a biocompatible water proof polymer such as neoprene, silicone, latex or artificial rubber for example.

Optionally, the internal unit 200 further comprises a power cell 260 for providing power. The power cell 260 is typically a single use disposable dry cell (battery) or a rechargeable battery. It may, however, be a chargeable capacitor. In some embodiments, the power cell 260 is a rechargeable battery that is rechargeable by induction.

Optionally, the at least one pressure sensor 210 (212) of the internal unit 200 is a piezoelectric sensor, such as a perovskite, that is configured to detect pressure applied to the one end of the internal unit. Other load cells may be used. In some embodiments, the at least one pressure sensor 210 of the internal unit is a piezoelectric sensor configured to detect pressure applied to an opposite end 270 (distal) of the internal device from that (proximal) to which the tail 240 is attached.

Optionally, the internal unit 200 further comprises a second pressure sensor 212 configured to detect pressure applied to the first end 250 (proximal to the tail 240) of the internal unit.

Figure 2:
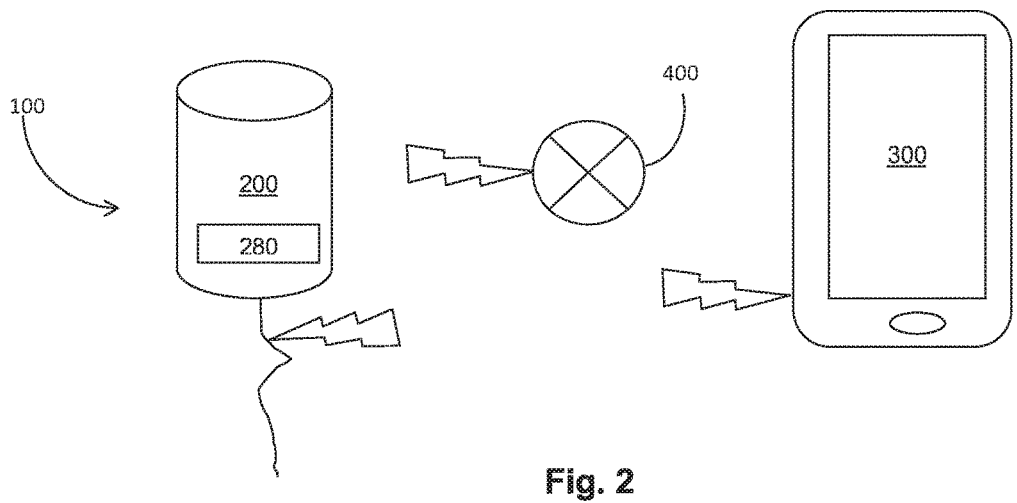
FIG. 2 is a schematic block diagram of a system of a second embodiment of the invention.

In some embodiments, the internal unit 200 further comprises a LED 275 and corresponding optical sensor 285, thereby enabling absolute movement forwards or backwards along the vaginal canal to be tracked. In some embodiments, the internal unit 200 further comprises an E.M.S. (Electrical Muscle Stimulation) system 290. EMS systems are predominately used to prevent, or reduce, muscle atrophy. Atrophy is the weakening and loss of muscle tone, which is usually experienced after surgeries or injuries. EMS has been proven to be an effective means of preventing muscle atrophy. EMS also helps by increasing blood flow to muscles, increasing range of motion, increasing muscle strength, as well as enhancing muscle endurance. EMS has pain management attributes in helping muscle related pain, such as a spastic muscle, sore muscles, or tight muscles. One type of EMS system is a Transcutaneous Electrical Nerve Stimulation (TENS) sensor. The TENS sensor may provide electrical signals to the vaginal muscle for active stimulation. Electrical stimulation is typically provided at frequencies of 10-50 Hz and in units of milli-amps and milli-seconds, with the impedance varying as necessary. However, stimulation at frequencies of up to 100 Hz are not unknown, and the internal device offering electromagnetic stimulation should support such frequencies. With respect to FIG. 2, a schematic block diagram of a system 1000 in accordance with a second embodiment of the invention is shown.

In the second embodiment 1000, the system includes an anchor 400 for attaching to the user, and the internal unit includes a distance sensor 280 for monitoring the separation of the anchor 400 from the internal unit 200. The anchor 400 may be attached to the body, for example to the buttocks or to the navel, by means of an adhesive strip or a vacuum sucker for example.

Figure 3:
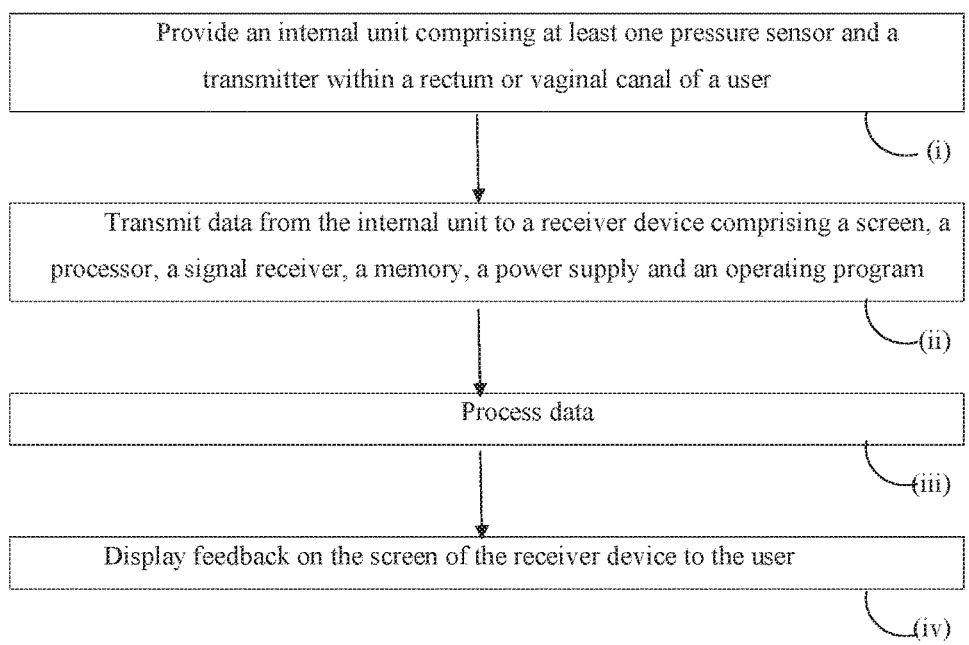
FIG. 3 is a flowchart of a method for exercising the pelvic region in accordance with one embodiment of the invention.

FIG. 3 is a flowchart of a method for exercising the pelvic region in accordance with one embodiment of the invention.

The method consists of: (i) providing an internal unit 200 comprising at least one pressure sensor 210 and a transmitter 220 within a rectum or vaginal canal of a user; (ii) transmitting data from the internal unit 200 to a receiver device 300 comprising a screen 310, a processor (320), a signal receiver 330, a memory 340, a power supply 350 and an operating program 360, and (iii) processing such data and (iv) displaying on the screen 310 information to the user regarding pressure on the internal unit 200.

Optionally, the internal unit 200 comprises two pressure sensors 210, 212 one at each end 250, 270, and the data displayed includes pressure differences between contraction forces applied to each end 250, 270.

In some embodiments, the internal unit 200 further comprises a distance sensor 280 for monitoring distance between the internal unit 200 and an external anchor 400 attached to anatomy of the user for monitoring movement of the internal unit 200 with respect to the external anchor 400.

In some embodiments, the internal unit 200 further comprises a LED 275 and corresponding optical sensor 285, enabling movement of the internal unit 200 with respect to the vaginal wall to be monitored.

In some embodiments, the internal unit 200 further comprises an E.M.S. (Electrical Muscle Stimulation) system 290. which may be a Transcutaneous Electrical Nerve Stimulation (TE NS) sensor for providing electrical signals to the vaginal muscle for active stimulation. Optionally, the internal unit further comprises a thermometer for transmitting a signal to the receiving unit. This may be useful for indicating ovulation to women trying to get pregnant or avoid pregnancy. It will be appreciated that a woman equipped with a smart phone 300 running an appropriate application 360 and with an internal unit 200 within her vaginal canal, and, if necessary, an anchor 400 stuck to her anatomy, such as to her buttock or to her navel, is able to practice pelvic floor exercises for short or long periods whilst commuting, at her desk, watching television, walking or exercising, whilst in bed and/or at other times during her daily routine.

In addition or instead of active exercise periods, the internal unit may communicate with the receiver unit 300 when an incident occurs. For example, the internal unit may provide messages when feeling a dilation of the vaginal canal or a dropping of the pelvis, whilst sneezing or during exercise, thereby helping a woman to tense her muscles and overcome this type of dilation or dropping which is a primary cause of urinary incontinence.

The GUI 310 of the smart-phone 300 may provide instructions to her and can, using signals from the internal unit 200, provide feedback as to whether or not she is exercising correctly, and can provide exercises to do, such as to tense pelvic muscles to thereby raise the floor of the pelvis. Thus embodiments of the present invention train the user to tense pelvic muscles and can help treat incontinence and can help avoid gym exercising and similar activities creating pelvic problems. The devices 200, 300, systems 100, 1000 and methods described can tighten vaginal muscle, providing more fulfilling sexual interaction to both partners, and can help the user to recover from birth.

The internal unit may further comprise additional sensors such as a temperature sensor that may be useful to indicate ovulation, chemical sensors for detecting pH, glucose levels for detecting diabetes, detectors for testosterone or estrogen for detecting pregnancy, and the like.

The GUI 310 may show numerical data, graphs comparing pressure at upper and lower ends of the internal unit, a graphic image schematically resembling the internal unit within the vaginal canal or a more user friendly and less scientific graphic image such as balloons, cartoon figures, and the like. Color changes or audible signals may be used to provide warning.

The external unit may communicate periodically with a central unit of a therapist or physician enabling professional supervision. However, one advantage of the present system over the prior art is that patients may work unsupervised when and where convenient to themselves, without potentially embarrassing and intrusive intervention. The system may be programmed to show improvement over time and to provide age and health/lifestyle appropriate targets for women after childbirth, for elderly patients with urinary incontinence and for other users. Persons skilled in the art will appreciate that the present invention is not limited to what has been particularly shown and described hereinabove. Rather the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A system for pelvic exercising by a user, the system comprising:
   an internal unit and a receiver device;
   the internal unit for positioning within a body cavity of the user; and
   comprising at least one pressure sensor and a transmitter within a housing;
   the receiver device comprising a GUI, a processor, a signal receiver, a memory, a power supply and an operating program, such that the receiver device receives data from the internal unit and displays information to the user, wherein the internal unit comprises means for monitoring tendency of the internal unit to move deeper into the body cavity in response to muscular exertion.

2. The system of claim 1 wherein the internal unit is substantially cylindrical.

3. The system of claim 1 wherein the internal unit has a length of 3 to 8 cm.

4. The system of claim 1 wherein the internal unit has a diameter of between 1 and 3 cm.

5. The system of claim 1 wherein the body cavity is selected from the group consisting of a vagina and a rectum.

6. The system of claim 1 wherein the means for monitoring tendency of the internal unit to move deeper into body cavity in response to muscular exertion comprises an anchor for attaching to the user, and a distance sensor for monitoring separation of the anchor from the internal unit.

7. The system of claim 6 wherein the anchor is attachable by an adhesive strip or a vacuum sucker to a buttock or a navel.

8. The system of claim 1 wherein the means for monitoring tendency of the internal unit to move deeper into body cavity in response to muscular exertion comprises a first piezoelectric sensor configured to detect pressure applied to a first end of the internal unit and a second pressure sensor configured to detect pressure applied to an opposite end of the internal unit.

9. The system of claim 1 wherein the means for monitoring tendency of the internal unit to move deeper into body cavity in response to muscular exertion comprises a movement sensor for monitoring movement along the vaginal canal.

10. The system of claim 9 wherein the movement sensor comprises a light emitting diode and corresponding light sensor.

11. The system of claim 1 wherein the internal unit further comprises a flexible tail that protrudes outside the body.

12. The system of claim 1 wherein the housing comprises a biocompatible water proof polymer typically selected from the group comprising neoprene, silicone, latex or artificial rubber.

13. The system of claim 1 wherein the internal unit further comprises at least one of:
   (i) a battery that is rechargeable by induction,
   (ii) an Electrical Muscle Stimulation (E.M.S.) system, and
   (iii) a non-rechargeable battery.

14. The system of claim 1 wherein the data signals comprise at least one of:
   a. data from at least one pressure sensor of the internal unit;
   b. data corresponding to a distance of the internal unit from an anchor positioned on external anatomy of the user, and
   c. data corresponding to an absolute movement of the internal unit within a body cavity.

15. An internal unit for the system of claim 1 being substantially cylindrical and having a length of 3 to 8 cm and a diameter of between 1 and 3 cm, for positioning within a body cavity of the user; and comprising at least one pressure sensor and a transmitter within a housing and means for monitoring tendency of the internal unit to move deeper into the body cavity in response to muscular exertion.

16. The system of claim 11 wherein the flexible tail that protrudes outside the body serves as an antenna for the transmitter.

17. The receiver device of claim 1 being a smart phone programmed with an application.

18. The receiver device of claim 1 further comprising a transmitter for transmitting signals for activating an E.M.S. (Electrical Muscle Stimulation) system in the internal unit.

19. A method of exercising a pelvis of a user comprising positioning an internal unit of claim 6 within a body cavity; attaching an anchor to anatomy of a user, and monitoring movement of the internal unit with respect to the external anchor.

20. A method of exercising a pelvis of a user comprising positioning an internal unit of claim 8 within a body cavity; monitoring pressure at first and second pressure sensors; transmitting data corresponding to said pressures to the external unit, and displaying information regarding differential pressure between first and second pressure sensors.

21. A method of exercising a pelvis of a user comprising positioning an internal unit of claim 9 within a body cavity; sensing movement of the sensor within the body cavity; transmitting data corresponding to the movement to the external unit, and displaying information regarding differential pressure between first and second pressure sensors.

\* \* \* \* \*